United States Patent [19]

Kawashima et al.

[11] Patent Number: 5,376,541

[45] Date of Patent: Dec. 27, 1994

[54] **PROCESS FOR PRODUCTION OF 8,11-EICOSADIENOIC ACID USING *MORTIERELLA ALPINA***

[75] Inventors: Hiroshi Kawashima; Kengo Akimoto, both of Ibaraki; Hideaki Yamada; Sakayu Shimizu, both of Kyoto, all of Japan

[73] Assignee: Suntory Limited, Osaka, Japan

[21] Appl. No.: 953,044

[22] Filed: Sep. 29, 1992

[30] Foreign Application Priority Data

Sep. 30, 1991 [JP] Japan .................................. 3-251957

[51] Int. Cl.$^5$ ........................ C12P 7/40; C12P 7/62; C12P 7/64
[52] U.S. Cl. .................................. 435/136; 435/134; 435/135; 435/244; 435/255.1
[58] Field of Search ............... 435/134, 136, 189, 135, 435/244, 255.1

[56] References Cited

U.S. PATENT DOCUMENTS 4,916,066 4/1990 Akimoto et al. .................. 435/136
5,093,249 3/1992 Nakajima et al. .................. 435/135

FOREIGN PATENT DOCUMENTS 0273708 12/1987 European Pat. Off. ............... 7/64
0332423 3/1989 European Pat. Off. ............... 7/64
0322227 6/1989 European Pat. Off. ............ 435/134
0399494 5/1990 European Pat. Off. ............... 7/64
2268690 11/1990 Japan ............................ 435/134

OTHER PUBLICATIONS

Pollero, R. J. et al, "Biosynthetic transformations of the eicosa-8,11-dienoic acid in *Acanthamoeba castellanii*," *Chemical Abstracts*, vol. 89, No. 23, Dec. 4, 1978.
Patent Abstracts of Japan, unexamined applns. c field vol. 15, No. 231, Jun. 12, 1991 The Patent Office Japanese Govt., p. 148 C 840 No. 3-72 892 (Idemitsu Petrochem.).

*Primary Examiner*—Douglas W. Robinson
*Assistant Examiner*—L. Blaine Lankford
*Attorney, Agent, or Firm*—Burns, Doane, Swecker & Mathis

[57] ABSTRACT

A process for the production of 8,11-eicosadienoic acid or a lipid containing 8,11-eicosadienoic acid comprising the steps of, culturing a microorganism having an ability to produce an omega 9 type polyunsaturated fatty acid in a medium supplemented with a Δ5 desaturase inhibitor, or adding a Δ5 desaturase inhibitor to a medium in which said microorganism has been cultured and further culturing the microorganism to produce 8,11-eicosadienoic acid, or a lipid containing 8,11-eicosadienoic acid, and recovering the 8,11-eicosadienoic acid, or the lipid containing 8,11-eicosadienoic acid.

4 Claims, No Drawings

PROCESS FOR PRODUCTION OF 8,11-EICOSADIENOIC ACID USING *MORTIERELLA ALPINA*

BACKGROUND OF THE INVENTION

1. Field of the Invention

The present invention provides a process for the production of 8,11-eicosadienoic acid or lipid containing same, using a microorganism having an ability to produce an omega 9 type polyunsaturated fatty acid.

2. Related Art

It is known that omega 9 type polyunsaturated fatty acids such as mead acid, 8,11-eicosadienoic acid and the like are present as constituent fatty acids of tissues of an animal having essential fatty acid deficiency. However, since an amount of these fatty acids is very low, it is very difficult to isolate and purify them. Moreover, the presence of these fatty acids in the microbial field has never been known. Such type of polyunsaturated fatty acids can be a precursor of the leukotriene 3 group, and therefore biological activities thereof are potentially useful. Therefore, there is a need for the development of a process for producing a large amount of 8,11-eicosadienoic acid.

Accordingly, the present invention provides a simple and efficient process for the production of 8,11-eicosadienoic acid and lipid containing 8,11-eicosadienoic acid using an inexpensive culture medium with an additive such as a Δ5 desaturase inhibitor.

SUMMARY OF THE INVENTION

The present inventors, after various researches, have found that when a microorganism having an ability to produce an omega 9 type polyunsaturated fatty acid is cultured in the presence of Δ5 desaturase inhibitor etc., a ratio of mead acid is decreased and a ratio of 8,11-eicosadienoic acid is increased.

Accordingly, the present invention provides a process for the production of 8,11-eicosadienoic acid comprising the steps of:

culturing a microorganism having an ability to produce an omega 9 type polyunsaturated fatty acid in a medium supplemented with a Δ5 desaturase inhibitor or adding a Δ5 desaturase inhibitor into a medium in which said microorganism has been cultured and further culturing the microorganism to produce 8,11-eicosadienoic acid or a lipid containing 8,11-eicosadienoic acid; and recovering the 8,11-eicosadienoic acid.

The present invention further provides a process for the production of a lipid containing 8,11-eicosadienoic acid comprising the steps of:

culturing a microorganism having an ability to produce an omega 9 type polyunsaturated fatty acid in a medium supplemented with a Δ5 desaturase inhibitor, or adding a Δ5 desaturase inhibitor into a medium in which said microorganism has been cultured and further culturing the microorganism to produce a lipid containing 8,11-eicosadienoic acid; and recovering the lipid containing the 8,11-eicosadienoic acid.

The present invention moreover provides a process for the production of 8,11-eicosadienoic acid comprising the steps of:

culturing a microorganism having an ability to produce an omega 9 type polyunsaturated fatty acid in a medium supplemented with at least one additive selected from the group consisting of sesame oil, peanut oil, an extract obtained by extracting sesame oil with an organic solvent substantially immiscible with sesame oil, an extract of sesame seeds, an extract of Gokahi derived from a medicinal plant, an extract of *Acanthopanax gracilistylus* W. W. Smith, an extract of *Acanthopanax senticosus* Harms, an extract of *Acanthopanax henryi*, an extract of *Acanthopenax verticillatus* Hoo, an extract of Touboku derived from a medicinal plant, an extract of *Paulownia fortunei* Hemsl, an extract of *Paulownia tomentosa* Steud, an extract of Hakukajuhi derived from a medicinal plant, an extract of *Ginkgo biloba* L., an extract of Hihatsu derived from a medicinal plant, an extract of *Piper longum* L, an extract of Saishin (*Asiasari radix*) derived from a medicinal plant, an extract of *Asiasarum heterotropoides* var mandshuricum, an extract of *Asakum sieboldii* Mig, an extract of tarragon, an extract of dill seeds, an extract of parsley, an extract of turmeric and an extract of nutmeg, or adding said additive into a medium in which said microorganism has been cultured and further culturing the microorganism to produce 8,11-eicosadienoic acid or a lipid containing 8,11-eicosadienoic acid, and recovering the 8,11-eicosadienoic acid.

The present invention still more provides a process for the production of a lipid containing 8,11-eicosadienoic acid comprising the steps of:

culturing a microorganism having an ability to produce an omega 9 type polyunsaturated fatty acid in a medium supplemented with at least one additive selected from the group consisting of sesame oil, peanut oil, an extract obtained by extracting sesame oil with an organic solvent substantially immiscible with sesame oil, an extract of sesame seeds, an extract of Gokahi derived from a medicinal plant, an extract of *Acanthopanax gracilistylus* W. W. Smith, an extract of *Acanthopanax senticosus* Harms, an extract of *Acanthopanax henryi*, an extract of *Acanthopanax verticillatus* Hoo, an extract of Touboku derived from a medicinal plant, an extract of *Paulownia fortunei* Hemsl, an extract of *Paulownia tomentosa* Steud, an extract of Hakukajuhi derived from a medicinal plant, an extract of *Ginkgo biloba* L., an extract of Hihatsu derived from a medicinal plant, an extract of *Piper longum* L, an extract of Saishin (*Asiasari radix*) derived from a medicinal plant, an extract of *Asiasarum heterotropoides* var mandshuricum, an extract of *Asakum sieboldii* Mig, an extract of tarragon, an extract of dill seeds, an extract of parsley, an extract of turmeric and an extract of nutmeg, or adding said additive into a medium in which said microorganism has been cultured and further culturing the microorganism to produce a lipid containing 8,11-eicosadienoic acid; and recovering the lipid containing 8,11-eicosadienoic acid.

According to a preferred embodiment of the above-mentioned processes, the microorganism having an ability to produce omega 9 type polyunsaturated fatty acid has Δ5 desaturation activity and Δ6 desaturation activity, and having reduced or lost Δ12 desaturation activity. In another embodiment of the present processes, the microorganism having an ability to produce an omega 9 type polyunsaturated fatty acid has an ability to produce arachidonic acid (ARA) and has reduced or lost Δ12 desaturation activity.

DETAILED DESCRIPTION

In the present invention, any microorganisms having an ability to produce an omega 9 type polyunsaturated fatty acid can be used. More particularly, microorganisms having Δ5 desaturation activity and Δ6 desaturation activity, and having reduced or lost Δ12 desaturation activity can be used. Such microorganisms can be obtained, for example, by mutating a microorganism having an ability to produce ARA to generate a mutant having reduced or lost Δ12 desaturation activity.

Microorganisms having an ability to produce ARA include those belonging to the genus Mortierella, Conidiobolus, Pythium, Phytophthora, Penicillium, Cladosporium, Mucor, Fusarium, Aspergillus, Rhodotorula, or Entomophthora. As microorganisms belonging to the genus Mortierella, there are mentioned microorganisms belonging to the subgenus Mortierella, such as *Mortierella elongata*, *Mortierella exigua*, *Mortierella hygrophila*, *Mortierella alpina*, and the like. Microorganism used in the present invention, having an ability to produce 8,11-eicosadienoic acid can be obtained by mutating the microorganisms having an ability to produce ARA.

For mutagenesis, irradiation of a microorganism with a mutagen, such as radiation (X-ray, γ-ray, neutron or ultraviolet light), high temperature treatment, and chemical mutagens may be used. In a mutagenizing procedure, microbial cells are suspended in an appropriate buffer, and a mutagen is added therein. The treated suspension is incubated for an appropriate time, diluted and plated on a solid medium such as agar medium to form colonies of mutated microorganisms.

As chemical mutagens, alkylating agents such as nitrogen mustard, methyl methanesulfonate (MMS), N-methyl-N'-nitro-N-nitrosoguanidine (NTG); base analogs such as 5-bromouracil; antibiotics such as mitomycin C; base synthesis inhibitor such as 6-mercaptopurine; pigments such as proflavin; certain carcinogens such as 4-nitroquinoline-N-oxide; and others such as manganese chloride, potassium permanyanese, nitrous acid, hydrazine, hydroxylamine, formaldehyde, nitrofuran compounds may be mentioned. Microorganisms to be treated with mutagen can be vegetative cells such as mycelium or spores.

As a mutant belonging to the genus Mortierella, *Mortierella alpina* SAM 1861 (FERM BP-3590) can be used.

For culturing a mutant used in the present invention, spores, mycelium or a previously cultured preculture is added to a liquid medium or a solid medium. A liquid medium contains, as carbon source, glucose, fructose, xylose, saccharose, maltose, soluble starch, molasses, glycerol, mannitol, or the like, alone or in combination.

As a nitrogen source, organic nitrogen source such as peptone, yeast extract, malt extract, meat extract, casamino acids, corn steep liquor or urea, and an inorganic nitrogen source such as sodium nitrate, ammonium nitrate, ammonium sulfate or the like can be used alone or in combination. In addition, if necessary, inorganic salts such as phosphates, magnesium sulfate, ferric or ferrous sulfate, cupric sulfate or the like, and minor nutrient components such as vitamins may be used.

Concentration of components in a culture medium should be such that it does not inhibit the growth of microorganism. Generally and practically, a concentration of carbon source is 0.1 to 30% by weight, preferably 1 to 10% by weight, and a concentration of nitrogen source is 0.01 to 5% by weight, and preferably 0.1 to 2% by weight. Temperature for culturing is 5° to 40° C., and preferably 20° to 30° C,; and a pH value of a medium is 4 to 10, and preferably 6 to 9. Culturing may be aeration/agitation culturing, shaking culture, or stationary culture. Culturing is usually continued for 2 to 10 days.

In the case wherein a microorganism is cultured in a solid medium, the medium comprises wheat bran, rice hulls, rice bran or the like supplemented with water in an amount of 50 to 100% by weight relating to a weight of solid material. Culturing is carried out at 5° to 40° C., preferably 20° to 30° C. for 3 to 14 days. In this case, the medium can contain nitrogen sources, inorganic salts, and minor nutrient components, such as those described above.

According to the present invention, to accelerate an accumulation of 8,11-eicosadienoic acid, a substrate of an omega 9 type polyunsaturated fatty acid can be added to a medium. As the substrates, hydrocarbons having 12 to 20 carbon atoms such as tetradecane, hexadecane and octadecane; fatty acid having 12 to 20 carbon atoms such as tetradecanoic acid, hexadecanoic acid and octodecancic acid, a salts thereof, for example, sodium salt or potassium salt; fatty acid esters having 12 to 20 carbon atoms in the fatty acid moiety, for example, lower alkyl ester such as methyl ester, ethyl ester, propyl ester of such a fatty acid; and a lipid containing such fatty acids as its components, for example, olive oil, palm oil, coconut oil may be mentioned. They are used alone or in combination.

In the present invention, as Δ5 desaturase inhibitors, there are mentioned dioxabicyclo[3.3.0] octane derivatives represented by the following formula (I):

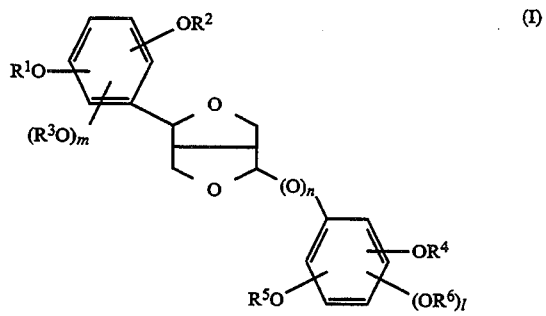

wherein $R^1$, $R^2$, $R^3$, $R^4$, $R^5$ and $R^6$ independently represent a hydrogen atom or an alkyl group having 1 to 3 carbon atoms, or $R^1$ and $R^2$, and/or $R^4$ and $R^5$ together form a methylene group or an ethylene group, and n, m and l are 0 or 1; piperonyl butoxide, curcumin, and compounds represented by the following formula (II):

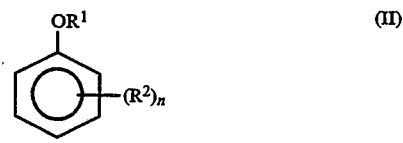

wherein $R^1$ represents a lower alkyl group; $R^2$ represents a hydroxyl group, an alkyl group, an alkoxy group, an alkenyl group or an oxyalkyl group wherein in the case that more than one $R^2$ is present, the $R^2$ may be the same or different; and n is an integer of 0 to 5. The lower alkyl group is selected from those having 1 to 6 carbon atoms, such as methyl, ethyl, isopropyl, n-propyl, n-buthyl, isobutyl, tert-buthyl, and the like. The alkyl group, the alkyl moiety in the alkaxy, oxyalkyl, and the alkenyl group have, preferably 12 to 20 carbon atoms. The Δ5 desaturase inhibitors can be used alone or in combination.

As the dioxabicyclo[3.3.0] octane derivative in the present invention, for example, sesamin, sesaminol, episesamin, episesaminol, sesamolin, 2-(3,4-methylenedioxyphenyl)-6-(3-methoxy-4-hydroxyphenyl)-3,7-dioxabicyclo-[3.3.0]octane, 2,6-bis-(3-methoxy-4-hydroxyphenyl)-3,7-dioxabicyclo[3.3.0]octane or 2-(3,4-methylenedioxy-phenyl)-6-(3-methoxy-4-hydroxyphenoxy)-3,7-dioxabicyclo[3.3.0]octane can be used. These derivatives can be used alone or in the form of a mixture of two or more thereof. Both optically active form and racemic form can be used.

The dioxabicyclo[3.3.0]octane derivative, one of the Δ5 desaturase inhibitors of the present invention, for example, can be obtained by the following procedure. First, an extract composed mainly of the dioxabicyclo[3.3.0]octane derivatives can be obtained from sesame oil according to a method comprising extracting sesame oil with an organic solvent substantially immiscible with sesame oil and capable of extracting and dissolving the compound of the present invention, and concentrating the extract. As the organic solvent, there can be mentioned, for example, acetone, methylethylketone, diethylketone, methanol and ethanol. For example, an extract composed mainly of the compounds of the present invention can be obtained by mixing sesame oil homogeneously with an organic solvent as mentioned above, allowing the mixture to stand at a low temperature, carrying out a phase separation according to a customary process, and removing the solvent from the solvent fraction by evaporation.

More specifically, sesame oil is dissolved in 2 to 10 volumes, preferably 6 to 8 volumes of acetone, and the solution is allowed to stand at −80° C. overnight. As a result, the oil component is precipitated, and the organic solvent is removed from the obtained filtrate by distillation, whereby an extract composed mainly of the compounds of the present invention is obtained. Alternatively, sesame oil is mixed with hot methanol or hot ethanol, the mixture is allowed to stand at room temperature, and the solvent is removed from the solvent fraction to obtain an extract composed mainly of the compounds of the present invention. More specifically, sesame oil is mixed with hot methanol (higher than 50° C.) or hot ethanol (higher than 50° C.) in a volume 2 to 10 times, preferably 5 to 7 times, as large as the volume of the sesame oil to effect a violent extraction. The phase separation is effected by a phase separation when standing at room temperature or a centrifugal separation according to customary procedures, and the solvent is removed from the solvent fraction by distillation to obtain an extract composed mainly of the compounds of the present invention. Furthermore, the supercritical gas extraction can be utilized.

The compound of the present invention can be obtained from an extract as mentioned above by treating the extract by a customary method such as column chromatography, high performance liquid chromatography, recrystallization, distillation, or liquid-liquid countercurrent distribution chromatography. More specifically, by using a reversed phase column ($5C_{18}$) and methanol/water (60/40) as the eluent, the extract is subjected to high performance liquid chromatography, the solvent is removed by distillation, and the obtained crystal is recrystallized from ethanol to obtain the compound used in the present invention, such as sesamin, episesamin, sesaminol or episesaminol. The sesame oil used in the present invention can be either a purified product or a crude product. Furthermore, sesame seeds or sesame lees (defatted sesame seeds having a residual oil content of 8 to 10%) can be used. In this case, sesame seeds or sesame lees are pulverized if necessary, and then subjected to the extraction according to customary procedures using any solvent, for example, a solvent as mentioned above with respect to the extraction from sesame oil. The extraction residue is separated, and the solvent is removed from the extract by evaporation or the like to obtain an extraction product.

The compound used in the present invention, for example, sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane, can be obtained from a sesame seed extract, a sesame lee extract or a crude sesame oil extract according to the same procedures as described above. Moreover, the compound used in the present invention can be obtained from a by-product formed in the sesame oil-preparing process.

Note, sesamin obtained from *Asiasari radix* exhibits the same effects as those provided by sesame seeds, sesame bran and sesame oil.

The process for the purification of the compound used in the present invention and the process for obtaining the extract are not limited to those mentioned above, and the compound used in the present invention and the extract composed mainly of the compound of the present invention are not limited to those obtained from sesame oil, sesame lees and sesame seeds, but as is apparent to persons with ordinary skill in the art, all natural substances containing the compound used in the present invention can be used. For example, there can be mentioned Gokahi derived from a medicinal plant which is *Acanthopanax gracilistylus* W. W. Smith, *Acanthopanax senticosus* Harms, *Acanthopanax henryi* which is *Acanthopanax verticillatus* Hoo, Touboku derived from a medicinal plant which is *Paulownia fortunei* Hemsl or *Paulownia tomentosa* Steud, Hakukajuhi derived from a medicinal plant which is *Ginkgo biloba* L, Hihatsu derived from a medicinal plant which is *Piper longum* L, Saishin (*Asiasari radix*) derived from a medicinal plant which is *Asiasarum heterotropoides* var mandshuricum, or *Asarum sieboldii* Miq.

The following processes can be adopted for the synthesis of the dioxabicyclo[3.3.0]octane derivative.

For example, sesamin and episesamin can be synthesized according to the process of Beroza et al. [J. Am. Chem. Soc., 78, 1242 (1956)]. Pinoresinol [in the general formula (I), $R^1$ and $R^4$ represent H, $R^2$ and $R^5$ represent $CH_3$, and n, m and l are zero] can be synthesized according to the process of Freundenberg et al. [Chem. Ber., 86., 1157 (1953)]. Furthermore, syringaresinol [in the general formula (I), $R^1$ and $R^4$ represent H, $R^2$, $R^3$, $R^5$ and $R^6$ represent $CH_3$, n is zero, and each of m and l is 1] can be synthesized according to the process of Freundenberg et al. [Chem. Ber., 88, 16 (1955)].

The compound used in the present invention also can be used in the form of a glycoside, to accelerate absorption as far as the glycoside has a specific Δ5 desaturase inhibitory activity.

As embodiments of the compound represented by the formula (II), anisole, methoxyphenol, dimethoxybenzene, diethoxybenzene, trimethoxybenzene, methoxytoluene, 3(2)-tert-butyl-4-hydroxyanisole (BHA), eugenol, and the like can be mentioned.

Moreover, as additives added to a culture medium to increase an accumulation of 8,11-eicosadienoic acid, sesame oil, peanut oil, an extract obtained by extracting sesame oil with an organic solvent substantially immiscible in sesame oil, an extract of sesame seeds, an extract of Gokahi derived from a medicinal plant, an extract of *Acanthopanax gracilistylus* W. W. Smith, an extract of *Acanthopanax senticosus* Harms, an extract of *Acanthopanax henryi*, an extract of *Acanthopanax verticillatus* Hoo, an extract of Touboku derived from a medicinal plant, an extract of *Paulownia fortunei* Hemsl, an extract of *Paulownia tomentosa* Steud, an extract of Hakukajuhi derived from a medicinal plant, an extract of *Ginkgo biloba* L, an extract of Hihatsu derived from a medicinal plant, an extract of *Piper longum* L, an extract of Saishin (*Asiasari radix*) derived from a medicinal plant, an extract of *Asiasarum heterotropoides* var mandshuricum, an extract of *Asarum sieboldii* Miq, as well as extracts of spicy plants, such as an extract of tarragon, an extract of dill seeds, an extract of parsley, an extract of turmeric, an extract of nutmeg and the like. These extracts can be prepared using a solvent such as dichloromethane, ethanol, methanol, ethyl ether or the like.

An amount of the above-mentioned additives to be added to a culture medium is as follows. An amount of sesame oil or peanut oil or a total amount of them is 0.001 to 10% by weight per medium, and preferably 0.5 to 10% by weight per medium. An amount of a sesame oil extract and other extract to be added is $3 \times 10^{-3}$ to $3 \times 10^{-1}$% by weight per medium. An amount of a dioxabicyclo[3.3.0]octane derivatives such as sesamin, sesaminol, episesamin, episesaminol and the like, or a total amount of a combination thereof is $1 \times 10^{-3}$ to $1 \times 10^{-1}$% by weight per medium.

The additive can be added prior to the inoculation of a producer microorganism or immediately after the inoculation. Alternatively, the additive can be added, after culturing has started, to a culture medium in which the microorganism is growing or has been grown, followed by further culturing. Moreover, the additive can be added both prior to culturing and during culturing after culturing has started. In the case wherein the additive is added during culturing, the additive can be added once or more than one time, or continuously.

During the culturing, a large amount of lipid containing 8,11-eicosadienoic acid is intracellularly accumulated. In the case wherein a liquid medium is used, 8,11-eicosadienoic acid is then recovered by a procedure, for example, described in the following.

After the culturing, the cultured cells are recovered by a conventional solid liquid separation means, such as centrifugation or filtering. The cells are thoroughly washed with water, and preferably dried. The drying can be carried out by lyophilization or air drying. The dried cells are extracted with an organic solvent, preferably in a nitrogen gas flow. As an organic solvent, ether such as ethyl ether, hexane, a lower alcohol such as methanol or ethanol, chloroform, dichloromethane, petroreum ether, or the like can be used. Moreover, an alternating extraction with methanol and petroleum ether, or an extraction with a one phase solvent of chloroform-methanol-water can be successfully used. The solvent is distilled off from the extract under reduced pressure to obtain a lipid containing 8,11-eicosadienoic acid in a high concentration.

Alternatively, wet cells can be extracted with a solvent miscible with water, such as methanol or ethanol, or a mixed solvent miscible with water, comprising said solvent and water and/or another solvent. Other procedures are the same as described above for dried cells.

The lipid thus obtained contains 8,11-eicosadienoic acid as a component of the lipid such as fat. Although 8,11-eicosadienoic can be directly isolated, preferably it is isolated as an ester with a lower alcohol, for example, as methyl 8,11-eicosadienoate. The esterification accelerates the separation of the target fatty acid from other lipid components, and from other fatty acids produced during the culturing, such as parmitic acid, oleic acid and linoleic acid (these fatty acids are also esterified simultaneously with the esterification of 8,11-eicosadienoic acid). For example, to obtain methyl ester of 8,11-eicosadienoic acid, the above-mentioned extract is treated with anhydrous methanol/HCl 5 to 10%, or BF$_3$/methanol 10 to 50% at room temperature for 1 to 24 hours.

Methyl ester of 8,11-eicosadienoic acid is recovered preferably by extracting the above-mentioned treated solution with an organic solvent such as hexane, ether such as ethyl ether, ester such as ethyl acetate. Next, the resulting extract is dried on, for example, anhydrous sodium sulfate, and the solvent is distilled off preferably under reduced pressure to obtain a mixture comprising fatty acid esters. This mixture contains, in addition to methyl ester of 8,11-eicosadienoic acid, other fatty acid methyl esters, such as methyl parmitate, methyl stearate, methyl oleate and the like. To isolate methyl ester of 8,11-eicosadienoic acid from the mixture of these fatty acid methyl esters, column chromatography, low temperature crystallization, the urea-inclusion method, the liquid/liquid countercurrent chromatography method, and the like can be used alone or in combination.

To obtain 8,11-eicosadienoic acid from the methyl ester of 8,11-eicosadienoic acid, the latter is hydrolyzed with an alkali and 8,11-eicosadienoic acid is then extracted with an organic solvent, for example, an ether such as ethyl ether, an ester such as ethyl acetate, or the like.

Moreover, to recover 8,11-eicosadienoic acid without going through the methyl ester, the above-mentioned extracted lipid is subjected to an alkalysis (for example, with 5% sodium hydroxide at room temperature for 2 to 3 hours), and the alkal-hydrolysate is extracted and the desired fatty acid 8,11-eicosadienoic acid is purified according to a conventional procedure.

Next, the present invention is further explained by Examples.

EXAMPLE 1

2 ml of a medium (pH 6.0) containing 2% glucose, and 1% yeast extract, and a Δ5 desaturase inhibitor shown in Table 1 was put into a 10 ml Erlenmeyer flask and autoclaved at 120° C. for 20 minutes. A mutant, *Mortierella alpina* SAM1861 was added to the medium, and cultured on a reciprocating shaker (110 rpm) at 20° C. for 10 days.

After the culturing the cultured cells were recovered by filtration, thoroughly washed with water, and dried with a centrifuge evaporator (60° C., 2 hours). To the cells were added 2 ml methylene chloride and 2 ml anhydrous methanol/hydrochloric acid (10%), and the mixture was incubated at 50° C. for 3 hours to methylesterify fatty acids. 4 ml n-hexane and 1 ml water were added to extract fatty acid methyl esters. The extraction was repeated twice, and a combined organic extract was dried in a centrifuge evaporator at 40° C. for one hour so as to recover a fatty acid methyl ester preparation, which was then analyzed by gas chromatography. The result is shown in Table 1.

TABLE 1

| Additve (Concentration) | 8,11-Eicosadienoic acid produced (g/L) SAM1861 | Mead acid produced (g/L) SAM1861 |
|---|---|---|
| None additive | 0.05 | 0.25 |
| Sesame oil (1%) | 0.22 | 0.31 |
| Peanut oil (1%) | 0.18 | 0.37 |
| Ethanol extract of tarragon (0.1%) | 0.13 | 0.22 |
| Ethanol extract of turmeric (0.01%) | 0.14 | 0.23 |
| Sesamin (0.01%) | 0.26 | 0.21 |
| Sesaminol (0.01%) | 0.17 | 0.22 |
| Curcumin (0.01%) | 0.15 | 0.23 |
| Ethanol extract of Piper longum L (0.1%) | 0.13 | 0.22 |
| Ethanol extract of Acanthopanax gracilistylus (0.1%) | 0.12 | 0.24 |
| Ethanol extract of Asiasarum heterotropoides var. mandshuricum (0.1%) | 0.17 | 0.24 |

EXAMPLE 2

2.5 liters of a medium (Ph 6.0) containing 2% glucose, 1% yeast extract, and 0.01% sesamin or 0.1% ethanol extract of Asiarari radix was put into a 5 liter jar fermentor, and sterilized at 120° C. for 30 minutes. 40 ml of a preculture of *Mortierella alpina* mutant SAM1861 was added, and culturing was carried out at 24° C. and an aeraction rate of 1 vvm, for 7 days. 1% per medium of glucose was added daily for 2 to 5 days of the culturing. After the culturing, the cells were treated as described in Example 1 except that all procedures were carried out at a scale 500 times that of Example 1, so as to prepare a methyl ester preparation, which was then analyzed by gas chromatography. The result is shown in Table 2.

the structure of the product was confirmed by Mass spectrum, NMR analysis etc.

We claim:

1. A process for the production of 8,11-eicosadienoic acid comprising the steps of:
   culturing *Mortierella alpina* SAM 1861 (FERM BP-3590) in a medium supplemented with a Δ5 desaturase inhibitor, or adding a Δ5 desaturase inhibitor into a medium in which said microorganism has been cultured and further culturing the microorganism to produce 8,11-eicosadienoic acid, and recovering the 8,11-eicosadienoic acid.

2. A process for the production of 8,11-eicosadienoic acid according to claim 1, wherein the Δ5 desaturase inhibitor is selected from a group consisting of a dioxabicyclo[3.3.0]octane derivative represented by the following formula (I):

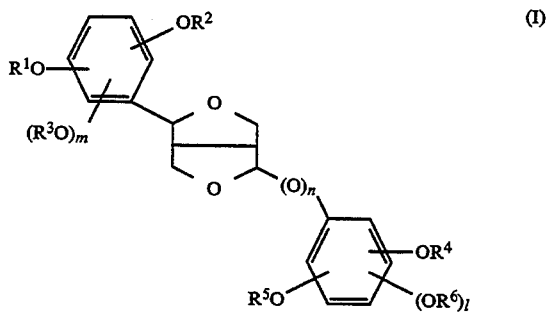

wherein $R^1$, $R^2$, $R^3$, $R^4$, $R^5$ and $R^6$ independently represent a hydrogen atom or an alkyl group having 1 to 3 carbon atoms, or $R^1$ and $R^2$, and/or $R^4$ and $R^5$ together form a methylene group or an ethylene group, and n, m and l are 0 or 1; piperonyl butoxide, curcumin, and a compound represented by the following formula (II):

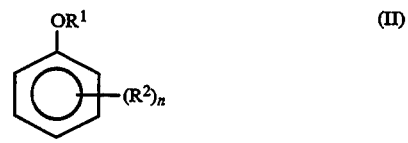

wherein $R^1$ is a lower alkyl group; $R^2$ is a hydroxy group, an alkyl group, an alkoxy group, an alkenyl group or oxyalkyl group wherein when more than one $R^2$ is present $R^2$ may be the same or different, and n is an integer of 0 to 5.

3. A process for the production of 8,11-eicosadienoic

TABLE 2

| Additives | Strains | 18:2 (ω9) produced (g/L) | Fatty acid composition (%) | | | | | | | | | | | | |
|---|---|---|---|---|---|---|---|---|---|---|---|---|---|---|---|
| | | | 16:0 | 18:0 | 18:1 | LA | 18:2 (ω9) | GLA | 20:1 | 20:2 | 20:2 (ω9) | 20:3 (ω9) | DGLA | Ara | 24:0 |
| None additive | SAM 1861 | 0.22 | 7.2 | 10.8 | 45.7 | 0 | 11.5 | 0 | 0.8 | 0 | 2.8 | 9.1 | 0 | 0 | 5.9 |
| Sesamin | SAM 1779 | 0.50 | 7.6 | 11.5 | 47.3 | 0 | 13.6 | 0 | 0.7 | 0 | 5.9 | 4.3 | 0 | 0 | 5.6 |
| Ethanol extract of Asiasari radix | SAM 1861 | 0.39 | 7.0 | 11.0 | 46.3 | 0 | 12.5 | 0 | 0.7 | 0 | 4.5 | 7.0 | 0 | 0 | 6.2 |
| | IFO 8568 | 0 | 8.1 | 3.6 | 27.5 | 8.8 | 0 | 5.8 | 0.6 | 0.7 | 0 | 0 | 10.9 | 25.3 | 4.81 |

*LA: linoleic acid, 18:2(ω9): 6,9-octadecadienoic acid, GLA: γ-linolenic acid, 20:2(ω9): 8, 11-eicosadienic acid, DGLA: dihomo-γ-linolenic acid, 20:3(ω9): meat acid, Ara: arachidonic acid From the fatty acid methyl ester mixture, 8,11-eicosadienoic acid was isolated by high performance liquid chromatography using a reverse column (5C18) and acetonitrile/water (85:15) as an eluting agent, and acid according to claim 2, wherein the dioxabicyclo[3.3.0]octane derivative is selected from a group consisting of sesamin, sesaminol, episesamin, episesaminol, sesamolin, 2-(3,4-methylenedioxyphenyl)-6-(3- methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane and 2-(3,4-methylenedioxyphenyl)-6-(3-methoxy-4-hydroxyphenoxy)-3,7-dioxabicyclo[3.3.0]octane.

4. A process for the production of 8,11-eicosadienoic acid comprising the steps of:

culturing *Mortierella alpina* SAM 1861 (FERM BP-3590) in a medium supplemented with at least one additive selected from the group consisting of sesame oil, peanut oil, an extract obtained by extracting sesame oil with an organic solvent substantially immiscible with sesame oil, an extract of sesame seeds, an extract of Gokahi derived from a medicinal plant which is *Acanthopanax gracilistylus* W. W. Smith, *Acanthopanax senticosus* Harms, *Acanthopanax henryi*, or *Acanthopanax verticillatus* Hoo, an extract of Touboku derived from a medicinal plant which is *Paulownia fortunei* Hemsl or *Paulownia tomentosa* Steud, an extract of Hakukajuhi derived from a medicinal plant which is *Ginkgo biloba* L, an extract of Hihatsu derived from a medicinal plant which is *Piper longum* L, an extract of Saishin (*Asiasari radix*) derived from a medicinal plant which is *Asiasarum heterotropoides* var mandshuricum or *Asarum sieboldii* Miq, an extract of tarragon, an extract of dill seeds, an extract of parsley, an extract of turmeric, and an extract of nutmeg, or adding said additive into a medium in which said microorganism has been cultured and further culturing the microorganism to produce 8,11-eicosadienoic acid, and recovering the 8,11-eicosadienoic acid.

* * * * *